United States Patent [19]

Miller

[11] Patent Number: 5,263,200
[45] Date of Patent: Nov. 23, 1993

[54] EYE PROTECTOR

[75] Inventor: Anne Miller, Harrow, Canada

[73] Assignee: Cool Eyes, Inc.

[21] Appl. No.: 353,058

[22] Filed: May 17, 1989

[51] Int. Cl.⁵ .......................... A61F 9/00; A61F 9/04
[52] U.S. Cl. ............................................ 2/15; 2/12
[58] Field of Search .................. 2/9, 12, 13, 426, 436, 2/439; 351/160 R

[56] References Cited

U.S. PATENT DOCUMENTS

| | | | |
|---|---|---|---|
| D. 191,140 | 8/1961 | Gates et al. | 351/160 R |
| D. 203,357 | 12/1965 | Adler | 351/160 X |
| D. 211,757 | 7/1968 | Urbach | 351/160 |
| 2,165,668 | 7/1939 | Vaccaro | 2/15 |
| 2,283,752 | 5/1942 | Gonsett | 2/15 |
| 2,527,947 | 10/1950 | Loos | 128/163 |
| 2,537,275 | 1/1951 | Malcom, Jr. | 2/436 |
| 2,715,223 | 8/1955 | Stegeman et al. | 2/436 X |
| 3,012,248 | 12/1961 | Kleenman | 2/436 |
| 3,020,552 | 2/1962 | Coon | 2/15 |
| 3,258,879 | 7/1966 | Edelstein | 351/160 X |
| 3,619,815 | 11/1971 | Towner, Jr. | 2/12 |
| 4,024,405 | 5/1977 | Szot | 250/516 |
| 4,055,378 | 10/1977 | Feneberg et al. | 351/160 R |
| 4,162,542 | 7/1979 | Frank | 2/15 |
| 4,211,476 | 7/1980 | Brummel et al. | 351/160 R |
| 4,411,263 | 10/1983 | Cook | 128/132 |
| 4,502,476 | 3/1985 | Welt | 128/132 X |
| 4,621,912 | 11/1986 | Meyer | 351/160 R |
| 4,642,816 | 2/1987 | Miller | 2/15 |
| 4,810,082 | 3/1989 | Abel, Jr. | 351/160 R |

*Primary Examiner*—Werner H. Schroeder
*Assistant Examiner*—Jeanette E. Chapman

[57] ABSTRACT

An eye protector having a body with an upper edge, a lower edge and an arcuate portion extending between the upper and lower edges. The body is dimensioned to fit over the eye so that, in doing so, the upper edge is positioned closely adjacent and above the eye while the lower edge is positioned closely adjacent and below the eye. The body is constructed so that the weight of the body between a midline extending across the arcuate section and the top edge of the body is greater than the remainder of the body. In addition, a plurality of spaced ridges extend outwardly from the anterior surface of the arcuate section which form cooling fins to cool the body. Ventilation holes are also formed in opposite lateral sides of the protector for cooling of the eyeball.

7 Claims, 1 Drawing Sheet

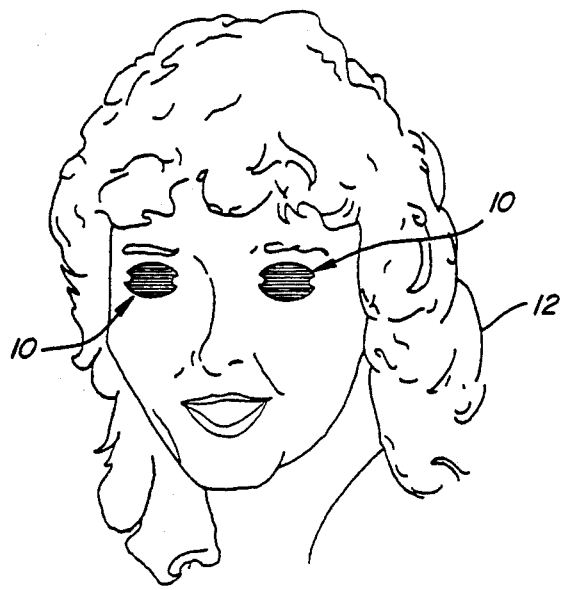
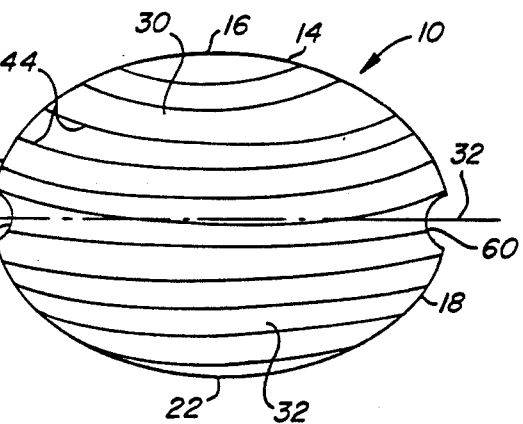
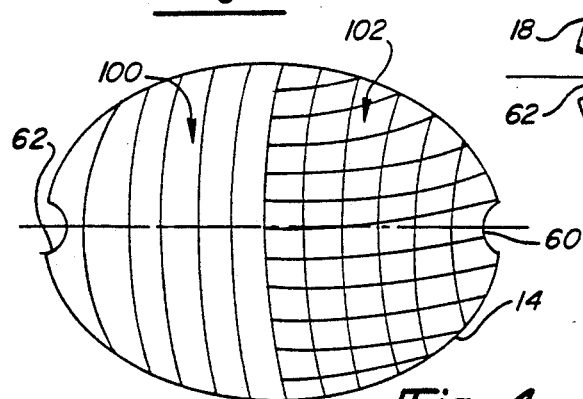
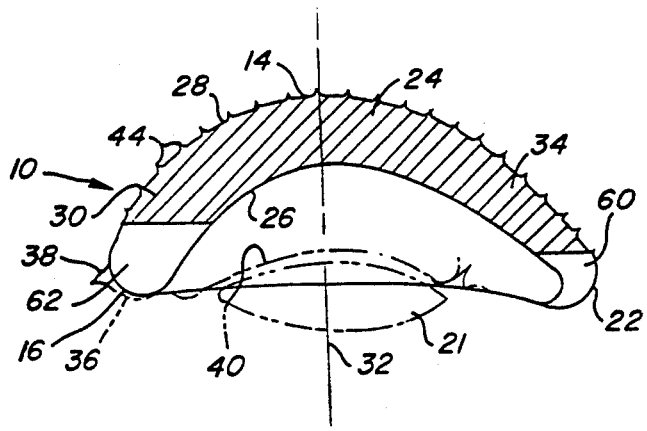

EYE PROTECTOR

BACKGROUND OF THE INVENTION

I. Field of the Invention

The present invention relates generally to eye protectors and, more particularly, to eye protectors for sun protection.

II. Background of the Invention

There are a number of previously known eye protectors which are used by sunbathers. These previously known eye protectors typically comprise a pair of opaque disks which are dimensioned so that one disk is positioned across and covers one eye while the other disk covers the other eye. Many of these previously known eye protectors further include a bridge which extends between and connects the two disks together so that both disks are installed and/or removed as a single unit.

These previously known eye protectors, however, have not proven wholly satisfactory in use. One disadvantage of these previously known eye protectors is that the wearer's eyes become heated underneath the eye protectors thereby resulting in discomfort.

A still further known disadvantage of these previously known eye protectors is that they become easily dislodged from the user's eye upon even small movement of the user's head. Although the previously known eye protectors with bridges minimize this problem, such eye protectors are disadvantageous in that they cover a portion across the user's nose. As a result, the covered portion of the nose does not become evenly tanned with respect to the user's face.

My prior U.S. Pat. No. 4,642,816 addressed many of the above problems However, with my prior device, the user's eyeballs became hot when used in very hot weather.

SUMMARY OF THE PRESENT INVENTION

The present invention provides an eye protector which overcomes all of the above mentioned disadvantages of the previously known devices.

In brief, the eye protector of the present invention comprises a body having an upper edge, a lower edge and an arcuate section extending between the upper and lower edges. The body is dimensioned so that, with the body positioned over one human eye, the upper edge is positioned closely adjacent and above the eye while the lower edge is positioned closely adjacent and below the eye. One separate eye protector is used for each eye.

Unlike the previously known eye protectors the thickness of the eye protector of the present invention decreases substantially continuously from its upper edge and to its lower edge. Consequently, the weight of the upper portion of the eye protector, i.e. the portion between a midline of the arcuate section and the upper edge, is greater than the remainder of the eye protector. In practice, it has been found that by increasing the weight of the upper portion of the eye protector with respect to its lower portion, the eye protector remains in place across the sunbather's eye despite even moderately rapid movements of the sunbather's head.

A plurality of spaced ridges protrude outwardly from the anterior surface of the arcuate section. These ridges form cooling fins which cool the body in use and, in doing so, maintain the sunbather's eye in a cool and comfortable state.

Any conventional material, such as porcelain, synthetics, plastics and the like can be used to form the body.

Ventilation openings are provided in the opposite lateral sides of the body. These ventilation openings provide cooling of the eyeball while still protecting the eyeball from solar radiation.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a perspective view illustrating a preferred embodiment of the present invention in use;

FIG. 2 is a front view illustrating the preferred embodiment of the invention;

FIG. 3 is a crossectional view taken substantially along line 3—3 in FIG. 2; and FIG 4 is a view similar to FIG. 2 but showing a modification thereof.

DETAILED DESCRIPTION OF A PREFERRED EMBODIMENT OF THE PRESENT INVENTION

With reference first to FIG. 1, a preferred embodiment of the eye protector of the present invention is thereshown and comprises a pair of eye protectors 10 adapted to be positioned over the eyes of a sunbather 12. The eye protectors 10 for both the right and left eyes are substantially mirror images to each other.

With reference now to FIGS. 2 and 3, the eye protector 10 is thereshown in greater detail and comprises a body 14 having an upper edge 16, side edges 18, and a lower edge 22. As best shown in FIG. 3, an arcuate section 24 having a concave posterior surface 26 and a convex anterior surface 28 extends continuously between the upper edge 16 and lower edge 22. Furthermore, the body 14 is dimensioned so that, with the body positioned over an eye as shown in FIGS. 1 and 3, the upper edge 16 abuts the sunbather's face closely adjacent to but above the eye 21 (FIG. 3) while, conversely, the lower edge 22 abuts against the sunbather's face below but closely adjacent the eye 21. In doing so, the concave posterior surface 26 of the arcuate section 24 is spaced outwardly from the user's eye 21.

With reference now particularly to FIG. 3, the thickness of the body 14 decreases substantially continually from the upper edge 16 and to the lower edge 22. Consequently, the weight of the upper half 30 of the body 14, i.e. the portion of the body 14 between a transverse midline 32 and the upper edge 16, is greater in weight than the lower half 34 of the body 14. In practice, it has been found that the heavier weight in the upper half 30 of the body 14 renders the eye protector 10 less susceptible to dislodgement despite relatively rapid movement of the sunbather's head. This occurs since the upper edge 16 of the body 14 nests within the natural cavity 36 (FIG. 3) formed between the sunbather's eyebrow 38 and upper eyelid 40.

Although in the preferred embodiment of the invention the thickness of the upper half 30 of the body 14 is greater than the lower half 34 to thereby increase the weight of the upper half 30, other means can be alternatively used to increase the weight of the upper half 30 of the body 14. For example, the body 14 can include weights (not shown) in its upper half 30 while maintaining a substantially constant body thickness between its upper edge 16 and lower edge 22.

With reference now to FIGS. 2 and 3, a plurality of spaced ridges 44 protrude outwardly from the anterior surface 28 of the body 14. These ridges 44 preferably extend transversely across the body 14 and form cooling fins to dissipate heat from the eye protector body 14. In practice, these cooling fins 44 have been found to keep the eye protector 10 relatively cool thereby maintaining the sunbather's eye in a cool and comfortable state. The anterior surface 28 is also preferably of a reflective color to minimize the heating of the eye protector 10 by radiant energy.

Although the ridges 44 preferably extend laterally across the body 14, as shown in FIG. 4, the ridges 44 can alternatively extend vertically, as shown at 100, or both vertically and laterally, as shown at 102. Furthermore, as shown in FIG. 4, any combination of vertical and/or lateral ridges can be used.

Referring now particularly to FIGS. 2 and 3, ventilation openings 60 and 62 are provided in the opposite lateral sides or edges 18 of the body 14. These ventilation openings 60 and 62 allow air circulation and air cooling of the user's eyes 40 while still protecting the eyes from solar radiation.

From the foregoing, it can be seen that the eye protector 10 of the present invention provides a simple and yet highly effective means for protecting a sunbather's eyes from radiant energy from the sun, sun lamps or the like.

Having described my invention, however, many modifications thereto will become apparent to those skilled in the art to which it pertains without deviation from the spirit of the invention as defined by the scope of the appended claims.

I claim:

1. An eye protector comprising:
   a body having an upper edge, a lower edge and an arcuate section extending between said upper and lower edges, said body being dimensioned so that, with said body positioned over a human eye, said upper edge is positioned closely adjacent and above the eye, said lower edge is positioned closely adjacent and below the eye, and said arcuate portion is spaced outwardly from and covers the eye,
   wherein said arcuate portion has a thickness which decreases substantially continuously from said upper edge to said lower edge,
   said body comprises an air ventilation opening on each lateral edge of the body.

2. The invention sa defined in claim 1 wherein said arcuate portion has a posterior surface adapted to face the eye and an anterior surface adapted to face away from the eye, and comprising a plurality of spaced ridges which protrude outwardly from said anterior surface.

3. The invention as defined in claim 2 wherein said ridges extend transversely across said anterior surface.

4. An eye protector comprising:
   a body having an upper edge, a lower edge and an arcuate section extending between said upper and lower edges, said body being dimensioned so that, with said body positioned over a human eye, said upper edge is positioned closely adjacent and above the eye, said lower edge is positioned closely adjacent and below the eye and said arcuate section is spaced outwardly from and covers the eye, and
   means for constructing said body so that the weight of said body between a transverse midline on said arcuate section and said top edge is greater than the weight of said body between said midline and said bottom edge,
   said body comprises an air ventilation opening on each lateral edge of the body.

5. An eye protector comprising:
   a body having an upper edge, a lower edge and an arcuate section extending between said upper and lower edges, said body being dimensioned so that, with said body positioned over a human eye, said upper edge is positioned closely adjacent and above the eye, said lower edge is positioned closely adjacent and below the eye and said arcuate section is spaced outwardly from and covers the eye, said arcuate section having an anterior surface and a posterior surface,
   means on said anterior surface for cooling said body,
   wherein said cooling means comprises a plurality of spaced ridges protruding outwardly from said anterior surface,
   said body comprises an air ventilation opening on each lateral edge of the body.

6. The invention as defined in claim 5 wherein said ridges extend laterally across said body.

7. The invention as defined in claim 5 wherein said ridges extend vertically across said body.

* * * * *